(12) United States Patent
Yang

(10) Patent No.: US 7,309,499 B2
(45) Date of Patent: Dec. 18, 2007

(54) FISH GELATIN HARD CAPSULE AND ITS PREPARATION METHOD

(75) Inventor: Joo Hwan Yang, Kyonggi-do (KR)

(73) Assignee: Suheung Capsule Co., Ltd., Kyonggi-do (KR)

( * ) Notice: Subject to any disclaimer, the term of this patent is extended or adjusted under 35 U.S.C. 154(b) by 777 days.

(21) Appl. No.: 10/716,405

(22) Filed: Nov. 20, 2003

(65) Prior Publication Data

US 2005/0069581 A1     Mar. 31, 2005

(30) Foreign Application Priority Data

Sep. 29, 2003    (KR) ...................... 10-2003-0067241

(51) Int. Cl.
     *A61K 9/64*          (2006.01)
     *A61K 9/48*          (2006.01)

(52) U.S. Cl. ...................... 424/456; 424/451
(58) Field of Classification Search ................ 424/451, 424/456

See application file for complete search history.

(56) References Cited

U.S. PATENT DOCUMENTS 6,423,346 B1 *    7/2002    Hansen et al.

FOREIGN PATENT DOCUMENTS

EP      0 346 879      * 12/1989

* cited by examiner

*Primary Examiner*—Humera N Sheikh
(74) *Attorney, Agent, or Firm*—Kenyon & Kenyon LLP

(57) ABSTRACT

The object of the present invention is to provide a process for preparing fish gelatin capsule comprising the steps of; i) preparing a mixed solution of pectin and glycerin; ii) adding said mixed solution to solubilized fish gelatin solution; iii) adding a small amount of calcium gluconate, sucrose fatty acid esters and glacial acetic acid to said mixture, iv) standing said mixture for adjusting viscosity and v) forming a fish gelatin capsule with obtained fish gelatin mixture, wherein said forming step comprises i) dipping the mold pin into the obtained fish gelatin mixture at the dipping pan, ii) molding the film of the fish gelatin capsule, iii) cooling said film of the fish gelatin capsule using 15~20° C. cooling air for 5~10 seconds at the bottom film cooling device, iv) cooling said film of the fish gelatin capsule again using 15~20° C. cooling air for 100~120 seconds at the upper film cooling device in order to control the flow of film.

2 Claims, 5 Drawing Sheets

FISH GELATIN HARD CAPSULE AND ITS PREPARATION METHOD

BACKGROUND OF THE INVENTION

The present invention relates to a hard capsule prepared by fish gelatin and its preparation method. More particularly, this invention relates to a hard capsule made by fish gelatin solution as base material; mixed solution of pectin and glycerin as gelling agent; and a small amount of calcium gluconate, sucrose fatty acid esters, glacial acetic acid as additive.

Further, the present invention also provides the method for preparing hard shell gelatin capsule made by fish gelatin and the apparatus for manufacturing hard shell gelatin capsule made by fish gelatin.

Gelatin is a protein of animal origin which has been known for a very long time and has numerous applications in the food, pharmaceutical, photographic and technical sectors. Gelatin is obtained industrially from the bones and skins of cattle and pigs, collected from abattoirs.

Gelatin has a good gelling property in a wide range of pH without support of additional ions or chemical agents. Further, the physical form of gelatin solution can be converted between gel and sol reversibly according to the change of temperature. Therefore, it has been used as a base material of hard capsule.

Recently, the gelatin extracted from bovine bone or pig skin has been avoided due to the risk of bovine spongiform encephalopathy (BSE) or religious causes. To replace it, the fish gelatin has been adopted as new base material of hard capsule.

Even though the physiochemical properties of fish gelatin are similar to those of bovine or pig gelatin in viscosity, strength and isoelectric point, the setting point, one of the important property of gelatin, of fish gelatin shows about 22° C. whereas the setting point of bovine or pig gelatin is about 27° C.

The reason why fish gelatin shows lower setting point is that the contents of hydroxyproline in fish gelatin is lower than that of bovine or pig gelatin. About 9% of hydroxyproline is contained in fish gelatin, whereas about 13~15% of hydroxyproline is contained in bovine or pig gelatin.

The lower setting point of fish gelatin results in lower gelling property of fish gelatin. Therefore, the fish gelatin solution laid on mold pin may flow outside of the mold pin due to its lower gelling property.

To solve above problem, a particular gelling agent shall be required to be adopted to fish gelatin solution.

In WO 2000/25760, carrageenan, tamarind seed, pectin, curdlan, gelatin, furcellaran, agar or gellan gum have been disclosed as a gelling agent for gelatin capsule. Further, pectin and glycerin have been also disclosed as a gelling agent in case of hydroxy propyl methyl cellulose (HPMC) capsule.

However, any gelling agent has not been disclosed for fish gelatin capsule.

SUMMARY OF THE INVENTION

The object of the present invention is to provide a process for preparing fish gelatin capsule comprising the steps of; i) preparing a mixed solution of pectin and glycerin; ii) adding said mixed solution to solubilized fish gelatin solution; iii) adding a small amount of calcium gluconate, sucrose fatty acid esters and glacial acetic acid to said mixture, iv) standing said mixture for adjusting viscosity and v) forming a fish gelatin capsule with obtained fish gelatin mixture, wherein said forming step comprises i) dipping the mold pin into the obtained fish gelatin mixture at the dipping pan, ii) molding the film of the fish gelatin capsule, iii) cooling said film of the fish gelatin capsule using 15~20° C. cooling air for 5~10 seconds at the bottom film cooling device, iv) cooling said film of the fish gelatin capsule again using 15~20° C. cooling air for 100~120 seconds at the upper film cooling device in order to control the flow of film.

The contents of fish gelatin mixed solution comprises 30~40 wt % of fish gelatin, 0.5~1.0 wt % of pectin, 0.01~0.05 wt % of glycerin, 0.1~0.5 wt % of calcium gluconate, 0.1~0.5 wt % of sucrose fatty acid esters and 0.01~0.05 wt % of glacial acetic acid as to total 100% of fish gelatin mixed solution.

The pectin used in this invention is low methoxyl amino pectin. Further, after cooling the film of the fish gelatin capsule, drying it in drying hood and cooling the mold pin to be below 2~4° C. for 4 minutes at the temperature controlling device.

※ Description of reference numerical

| | |
|---|---|
| 1. dipping pan | 2. Mold pin |
| 3. Bottom film cooling device | 4. Elevator for film adjustment |
| 5. Upper film cooling device | 6. Drying hood |
| 7. Temperature controlling device | 8. Forming part |
| 9. Greasing part | |

DETAILED DESCRIPTION OF THE INVENTION

In order to enhance the gelling property and physical property of fish gelatin capsule of the present invention, a novel gelling agent is introduced to fish gelatin mixed solution as first means for improving gelling property and additional mechanical devices, such as, film cooling device and temperature controlling device are mounted to conventional manufacturing apparatus for improving property. Using gelling agent, the fish gelatin solution dipped in mold pin is stably gelled. Finally, the fish gelatin capsule having equal film distribution and thickness can be obtained using additional mechanical device.

Pectin is selected as proper gelling agent for fish gelatin capsule. Even though the gelling property increases according to increase of the amount of pectin, the physical property of capsule declines according to increase of the amount of pectin. For example, the cutting shape is not so good as well as the cleavage of film results from unequal film distribution.

Therefore, the amount of pectin has to be restricted to avoid physical drawbacks of fish gelatin capsule unlike HPMC capsule. It requires the improvement of manufacturing machine to be stably gelled by pectin. To obtain the equal film distribution, the temperature controlling device of mold pin and the film cooling device are required to be mounted in conventional manufacturing apparatus.

Fish gelatin mixed solution comprising 30~40 wt % of fish gelatin, 2.0~3.0 wt % of pectin, 0.01~0.05 wt % of glycerin, 0.1~0.5 wt % of calcium gluconate, 0.1~0.5 wt % of sucrose fatty acid esters and 0.01~0.05 wt % of glacial acetic acid as to total 100% of fish gelatin mixed solution was prepared. Then, this mixed solution is laid on dipping pan adjusting the temperature below 48° C.

The mold pin is dipped into dipping pan and formed gelatin film is dried using drying hood. Then, this molded film is stripped, adjusted in length, cut and jointed in order to make a fish gelatin capsule. However, the molded gelatin film by molding pin shows a bad cutting shape with scraps of film, which causes the decline of fish gelatin capsule's physical properties.

We found that this problem occurs due to the increase of pectin amount. Even if the physical property of capsule is improved according to minimizing pectin amount, the gelling property of mixed solution is declined not to prepare desirous formation of capsule.

Through the repeated experiments, we found that the desirable pectin amount is 0.5~1.0 wt %. However, secondary means are required to overcome the lack of gelling property of gelatin capsule dipped in molding pin.

Figure 1:
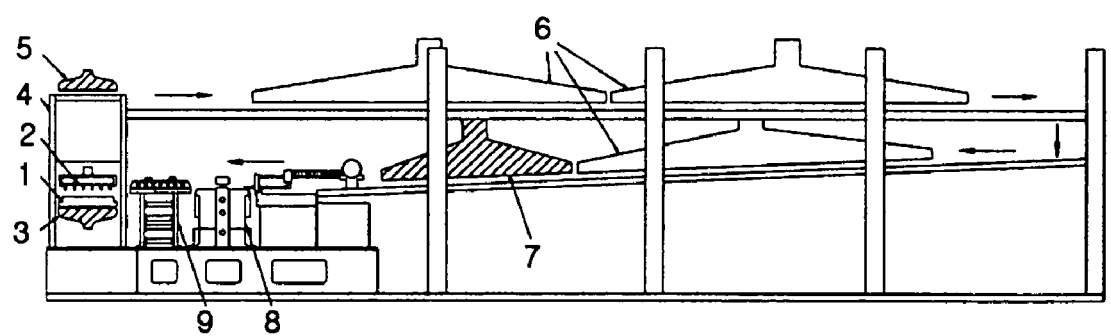
FIG. 1 shows a schematic view of manufacturing apparatus for fish gelatin capsule of present invention.
Figure 2:
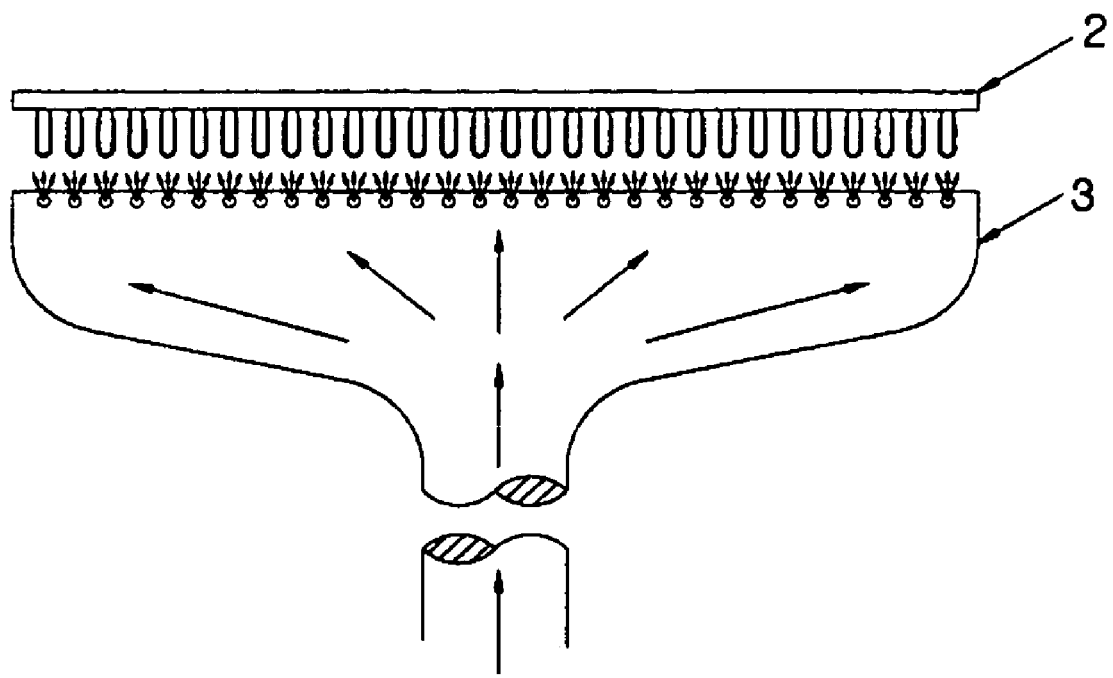
FIG. 2 shows a enlarged view of bottom film cooling device for gelling the formed film in FIG. 1.
Figure 3:
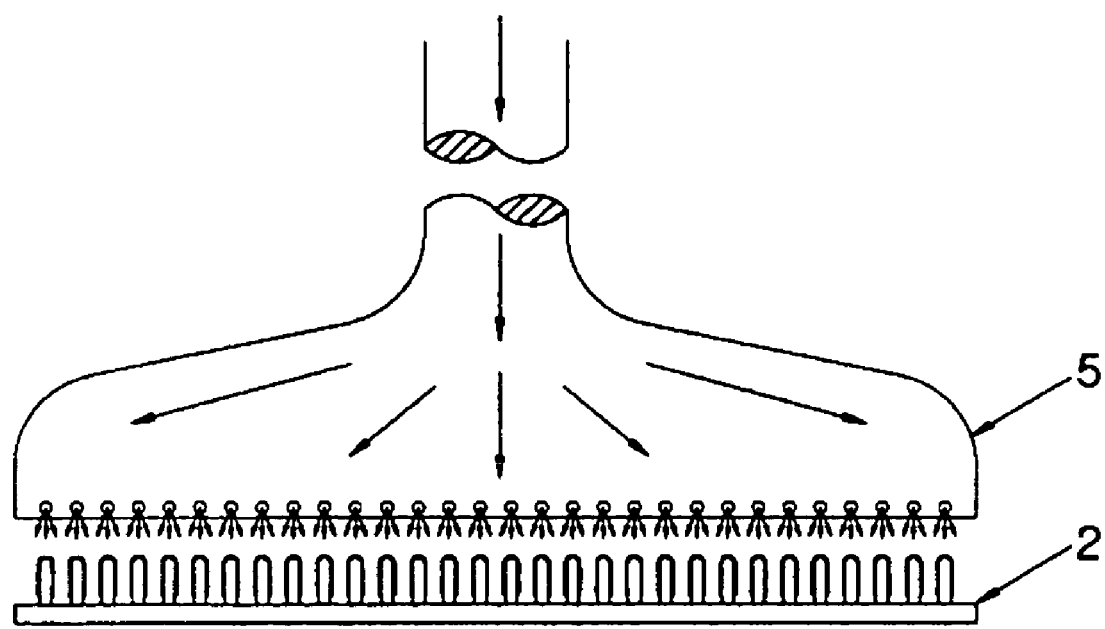
FIG. 3 shows a enlarged view of upper film cooling device for gelling the formed film in FIG. 1.
Figure 4:
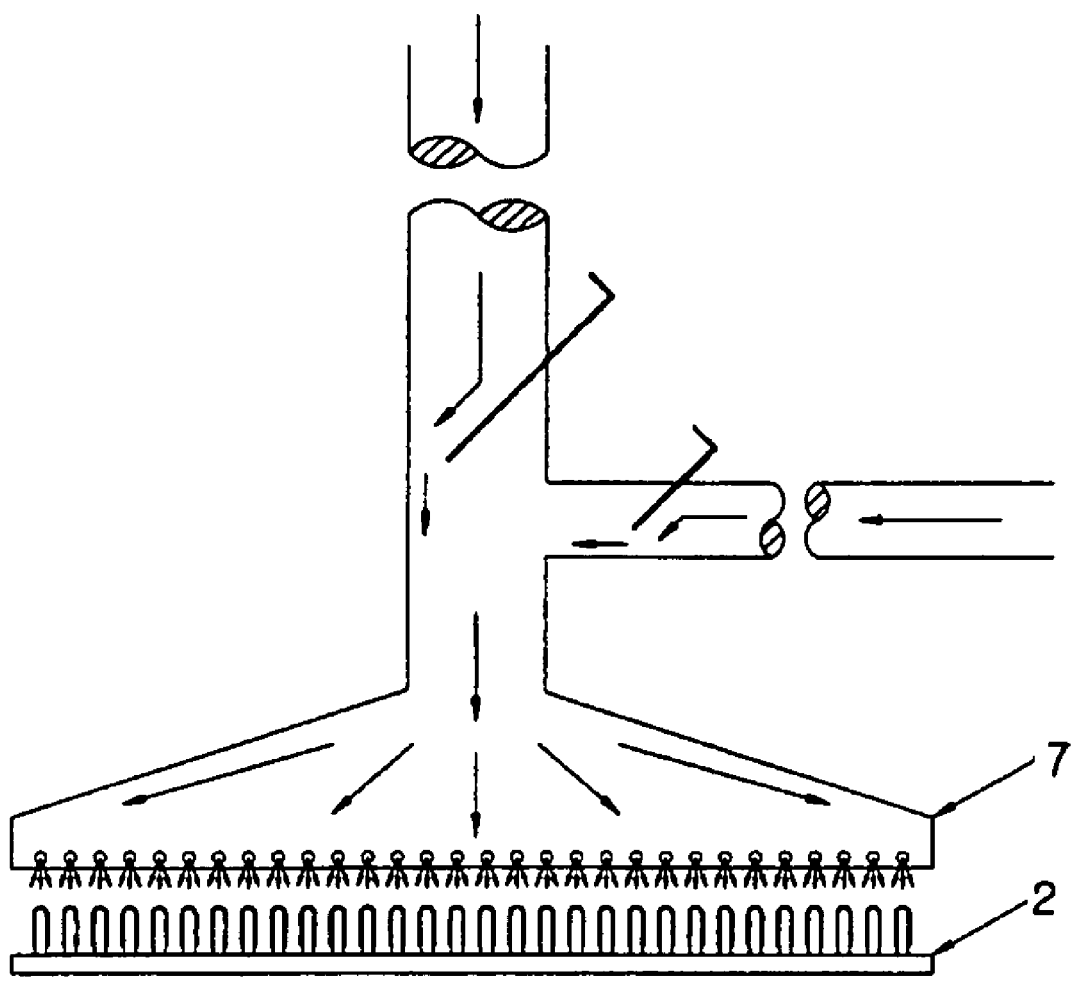
FIG. 4 shows a enlarged view of temperature controlling device for cooling the mold pin before dipping in FIG. 1.

Therefore, we adopted the experimental fact that gelling property increases according to the decline of gelatin film temperature. Then, the temperature controlling device (7) is introduced to decline the temperature of molding pin below 2~4° C. compared to conventional temperature of molding pin (see FIG. 4). Further, the bottom film cooling device (3) and the upper film cooling device (5) are also mounted in order to decline the temperature of gelatin film (see FIG. 2 and FIG. 3). Using the bottom film cooling device, the gelatin film is cooled by cooled air at 5~10 seconds and using the upper film cooling device, the gelatin film is cooled by cooled air at 100~120 seconds. Finally, excellent fish gelatin film is obtained.

Then, the fish gelatin capsule is manufactured in a same manufacturing process, for example, drying in hood, stripping, adjustment in length, cut and jointing process. The outlook and physical property of obtained fish capsule are excellent, such as, the shape of cutting, film thickness and distribution and weight of film.

The present invention can be explained by following examples. However, the scope of present invention shall not be limited to following examples.

EXAMPLE 1

Preparation of Fish Gelatin Capsule

Step 1: Preparation of Fish Gelatin Aqueous Solution 33 kg of fish gelatin (concentration: 33.0%) is slowly added to 57.524L of purified water of 65~70° C. Then, the solution is stirred for 120 minutes with 300 rpm until complete dispersion. After raising the temperature up to 55~60° C. for solubilizing the solution, the solution is cooled for 4~8 hours in room temperature.

Step 2: Preparation of Pectin and Glycerin Mixed Solution

The mixed solution of pectin and glycerin is prepared by following method. 825 g of pectin (concentration: 0.825%) is slowly added to 6.3 L of purified water at 60° C. Then, the mixture is stirred with 8,000 rpm until complete dispersion using mixer. After complete solubilization of pectin, 33 g of glycerin (concentration: 0.033%) is added and stirred for 5 minutes for preparing pectin and glycerin mixed solution.

Prepared mixed solution is added to fish gelatin aqueous solution in step 1.

Step 3: Preparation of Fish Gelatin Mixed Solution

In next step, 165 g of calcium gluconate (concentration: 0.165%) is slowly added to 1.8 L of purified water at 60° C. Then, the mixed solution is stirred with 3,000 rpm for 3 minutes until complete dispersion using mixer, and the fish gelatin mixed solution in step 2 is added and stirred for 2 minutes. 330 g of sucrose fatty acid esters (concentration: 0.33%) and 23.1 g of glacial acetic acid (concentration: 0.0231%) are added to above solution, and the mixed solution is stirred for 10 minutes. Finally, fish gelatin mixed solution is prepared after adding the mixed solution.

Step 4. Film Formation Fish gelatin mixed solution obtained in step 3 is packed in vessel and stands still for adjusting the viscosity for 6~10 hours until the proper temperature of 46~48° C. The bubbles in the solution is removed and the solution is laid on dipping pan. After dipping the mold pin into dipping pan for 10~15 seconds, the film is transferred to bottom film cooling device for cooling for 5~10 seconds. Then, the film is transferred to upper film cooling device for cooling for 100~120 seconds. The temperature of cooling air is 15~20° C. with air velocity 4~6 m/sec. Then, formed film is transferred and dried in drying hood at 25~30° C. for 40~50 minutes and the film is laid on temperature controlling device to decline the temperature of mold pin below 2~4° C. for about 4 minutes compared to conventional temperature. The temperature of temperature controlling device is 17~20° C. with air velocity 6~8 m/sec. Finally, the fish gelatin capsule is manufactured in a same manufacturing process, for example, drying in hood, stripping, adjustment in length, cut and jointing process. The outlook and physical property of obtained fish gelatin capsule are excellent, such as, the shape of cutting, film thickness and distribution and weight of film.

EXAMPLE 2

Comparison Between Fish Gelatin Capsule and Conventional Gelatin Capsule

The experiment is carried out for comparison of properties between fish gelatin capsule and conventional gelatin capsule.

The table 1 shows the film distribution of cap between fish gelatin capsule and conventional gelatin capsule.

TABLE 1

|  | fish gelatin(mm) | conventional gelatin(mm) |
| --- | --- | --- |
| CE | 0.101 | 0.101 |
| Dome | 0.108 | 0.110 |
| Shoulder | 0.079 | 0.077 |
| Top | 0.127 | 0.130 |

The table 2 shows the film distribution of body between fish gelatin capsule and conventional gelatin capsule.

TABLE 2

|  | fish gelatin(mm) | conventional gelatin(mm) |
|---|---|---|
| CE | 0.101 | 0.103 |
| Dome | 0.110 | 0.108 |
| Shoulder | 0.082 | 0.080 |
| Top | 0.122 | 0.128 |

There has been no significant difference in film distribution between fish gelatin capsule and conventional gelatin capsule. Therefore, there is no problem in manufacturing fish gelatin capsule.

Figure 5:
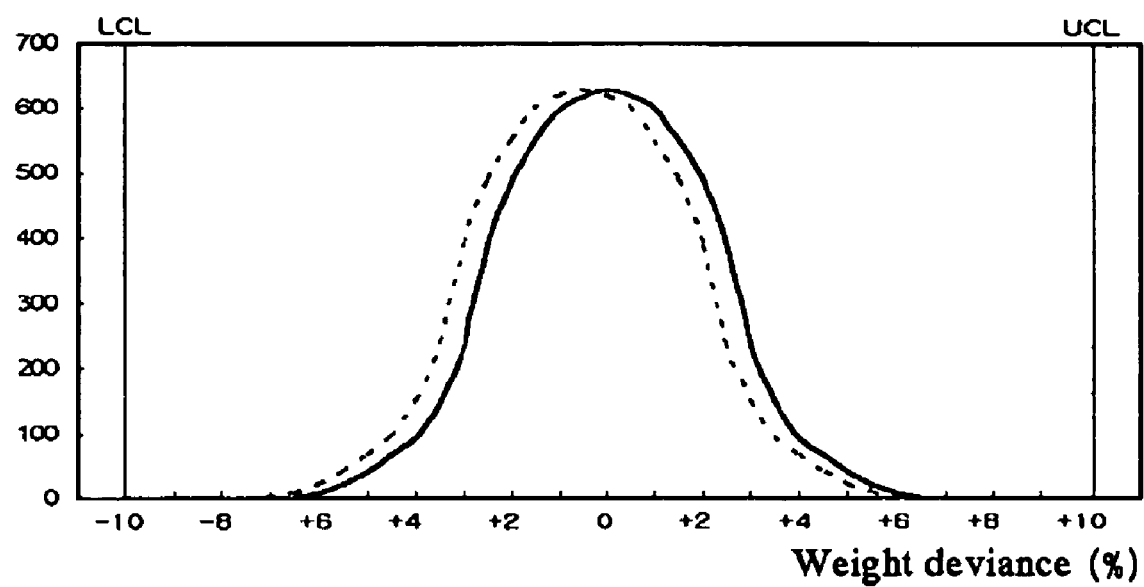
FIG. 5 shows the comparison of weight deviation between fish gelatin capsule of present invention and conventional gelatin capsule.

FIG. 5 shows the comparison of weight deviation between fish gelatin capsule of present invention and conventional gelatin capsule. As shown in FIG. 5, there is no significant difference in weight deviation between fish gelatin capsule and conventional gelatin capsule. The weight deviation belongs to ±10% weight range.

The present invention accomplishes the manufacturing fish gelatin capsule using pectin and glycerin as gelling agent. Further, additional cooling device is adopted for better physical property of capsule of the present invention.

What is claimed is:

1. A process for preparing a fish gelatin capsule comprising the steps of:
    i) preparing 100 wt part of an aqueous solution containing 30~40 wt part of a solubilized fish gelatin;
    ii) adding a mixed solution of 0.5~1.0 wt part of pectin and 0.01~0.05 wt part of glycerin to the solubilized fish gelatin solution;
    iii) adding 0.1~0.5 wt part of calcium gluconate, 0.1~0.5 wt part of sucrose fatty acid esters and 0.01~0.05 wt part of glacial acetic acid to the admixture resulting from step ii);
    iv) standing said admixture for adjusting viscosity; and
    v) forming a fish gelatin capsule,
    wherein said forming step comprises a) dipping the mold pin into the obtained fish gelatin mixture at the dipping pan, b) molding the film of the fish gelatin capsule, c) cooling said film of the fish gelatin capsule using 15~20° C. cooling air for 5~10 seconds at the bottom film cooling device, d) cooling said film of the fish gelatin capsule again using 15~20° C. cooling air for 100~120 seconds at the upper film cooling device in order to control the flow of film.

2. The process for preparing fish gelatin capsule according to claim 1, further comprising i) cooling the film of the fish gelatin capsule; and ii) drying it in drying hood and cooling the mold pin to be below 2~4° C. for 4 minutes at the temperature controlling device.

* * * * *